United States Patent
Buchberger

(10) Patent No.: US 8,752,545 B2
(45) Date of Patent: Jun. 17, 2014

(54) INHALER COMPONENT

(75) Inventor: Helmut Buchberger, Ennsdorf (AT)

(73) Assignee: BATMark Limited, London (GB)

( * ) Notice: Subject to any disclaimer, the term of this patent is extended or adjusted under 35 U.S.C. 154(b) by 0 days.

(21) Appl. No.: 13/984,512

(22) PCT Filed: Feb. 2, 2012

(86) PCT No.: PCT/AT2012/000017
§ 371 (c)(1),
(2), (4) Date: Aug. 29, 2013

(87) PCT Pub. No.: WO2012/106739
PCT Pub. Date: Aug. 16, 2012

(65) Prior Publication Data
US 2013/0333700 A1  Dec. 19, 2013

(30) Foreign Application Priority Data

Feb. 11, 2011 (AT) .................................. A 187/2011
Jul. 27, 2011 (AT) ................................ A 1095/2011

(51) Int. Cl.
*A61M 15/00* (2006.01)
*A61M 16/00* (2006.01)
*F24F 6/08* (2006.01)

(52) U.S. Cl.
USPC ............ 128/204.13; 128/203.12; 128/204.17; 392/395

(58) Field of Classification Search
CPC ... A24F 47/008; A24F 47/004; A24F 47/002; A61M 1/2077; A61M 16/18; A61M 16/104; A61M 16/16; A61M 15/00; A61M 15/08; A61L 9/037; A61L 9/03; F24F 6/10
USPC ............ 128/204.23, 203.12, 203.15–203.16, 128/203.19, 203.21, 203.26–203.27, 128/202.21, 204.17; 131/270, 273, 194; 392/386, 394–397, 403–406
See application file for complete search history.

(56) References Cited

U.S. PATENT DOCUMENTS

| 5,121,881 A | * | 6/1992 | Lembeck | ................. 239/44 |
| 6,155,268 A | * | 12/2000 | Takeuchi | ................. 131/273 |
| 2011/0226236 A1 | | 9/2011 | Buchberger | |

FOREIGN PATENT DOCUMENTS

| EP | 0893071 A1 | 1/1999 |
| EP | 2018886 A1 | 1/2009 |
| WO | 2010/045671 A1 | 4/2010 |

OTHER PUBLICATIONS

International Search Report and Written Opinion, mailed Jul. 3, 2012 for International Patent Application No. PCT/AT2012/000017, filed Feb. 2, 2012. [with Machine Translation].
Written Opinion [WIPO English Translation], mailed Jul. 3, 2012 for International Patent Application No. PCT/AT2012/000017, filed Feb. 2, 2012.

* cited by examiner

*Primary Examiner* — Rachel Young
(74) *Attorney, Agent, or Firm* — N W Poulsen; L A Pinol

(57) ABSTRACT

The invention relates to an inhaler component for forming a vapor-air mixture and/or condensation aerosol by vaporising a liquid material and optionally condensing the vapor formed, including: a heating element for vaporising a portion of the liquid material; a wick for automatically supplying the liquid material to the heating element, wherein the wick comprises at least two end sections arranged apart from each other; a first capillary gap for automatically supplying the liquid material to the wick, wherein a first end section of the wick projects into the first capillary gap. In order that the heating element can be supplied more quickly and more reliably with the liquid material, a second capillary gap is provided, which receives therein the second end section of the wick.

22 Claims, 8 Drawing Sheets

INHALER COMPONENT

CLAIM FOR PRIORITY

This application is a National Stage Entry entitled to and hereby claims priority under 35 U.S.C. §§365 and 371 to corresponding PCT Application No. PCT/AT2012/000017, entitled "Inhaler Component," filed Feb. 2, 2012, which in turn claims priority to Austrian Patent Application No. A187/2011, filed Feb. 11, 2011, and to Austrian Patent Application No. A1095/2011, filed Jul. 27, 2011. The entire contents of the aforementioned applications are herein expressly incorporated by reference.

The invention relates to an inhaler component for the formation of a vapour-air mixture or/and of a condensation aerosol by evaporating a liquid material and, if necessary, condensing the vapour formed, comprising:

a heating element for the evaporation of a portion of the liquid material;

a wick for the automatic supply of the heating element with the liquid material, the said wick having at least two end sections arranged at a distance from each other;

a first capillary gap for the automatic supply of the wick with the liquid material, wherein a first end section of the wick extends into the first capillary gap.

DEFINITION OF TERMS

In the present patent application the term "inhaler" refers to medical as well as non-medical inhalers. The term refers furthermore to inhalers for the administration of drugs and materials which are not declared as drugs. The term refers, in addition, to smoking articles and cigarette substitutes, such as those in European patent class A24F47/00B, for example, as far as these are intended to supply the user with a vapour-air mixture or/and a condensation aerosol. The term "inhaler" also implies no restrictions on how the vapour-air mixture or/and condensation aerosol formed is supplied to the user or his body. The vapour-air mixture or/and condensation aerosol can be inhaled into the lungs or, in addition, only supplied to the oral cavity—without inhalation into the lungs.

"Capillary gap" means any gap which causes liquid transport solely on the basis of the capillary action of its confining walls. Wicks, wrapped wicks or channels filled with wick material are not capillary gaps.

WO 2010/045671 (Helmut Buchberger) describes an inhaler component for the intermittent, inhalation or pull-synchronous formation of a vapour-air mixture or/and condensation aerosol, consisting of (FIGS. 9 to 12 and FIGS. 17 to 18) a housing 3, a chamber 21 provided in the housing 3, an air intake opening 26 for the supply of air from the environment into the chamber 21 and an electric heating element for the evaporation of a portion of a liquid material 16, in which case the vapour formed mixes in the chamber 21 with the air supplied by the air intake opening 26 and the vapour-air mixture or/and condensation aerosol is or are formed. Furthermore, the inhaler component comprises a wick with a capillary structure, which wick forms with the heating element a laminar composite 22 and automatically resupplies the heating element with the liquid material 16 after evaporation. At least one heated section of the composite 22 is arranged without contact in the chamber 21 and the capillary structure of the wick lies exposed to a large extent in the said section at least on one side 24 of the laminar composite. One end of the laminar composite 22 projects into a capillary gap 41, which is coupled or is capable of being coupled by capillary to a liquid container 4 containing the liquid material 16. The capillary gap 41 draws the liquid material 16 from the liquid container 4 and conveys it to the wick.

After evaporation or inhalation the user of the inhaler component must observe a waiting period, during which the liquid material 16 can again completely infiltrate the wick. Evaporations before the expiration of the waiting period can lead to various disadvantageous consequences, for example a decrease in the given aerosol quantity or/and a local overheating of the wick, possibly associated with a decomposition of the liquid material and a degradation of the organoleptic characteristics of the vapour-air mixture or aerosol formed. In prototypes based on highly diluted ethanol or/and aqueous nicotine solutions, it was possible to obtain complete infiltration of the wick within 10 s. If the inhaler component is used as a cigarette replacement, then a waiting period of 10 s may be acceptable for many smokers; for some smokers, however, it may be too long. Furthermore, with the same prototypes it has been shown that even when the waiting period mentioned is adhered to, disturbances of the infiltration can occur. These disturbances rarely arise, but can lead to the same disadvantageous consequences as described above. The disturbances are characterized by an unsatisfactory wetting of the capillary structure of the wick by the liquid material and occur preferably locally, in regions of the wick which are peripheral in relation to the capillary gap.

The object of the invention is to remedy the aforementioned disadvantages of the arrangement known from the state of the art. More particularly, it is the object of the invention to design an inhaler component of the type described in the preamble in such a way that the wick is infiltrated with the liquid material as rapidly as possible and no unpleasantly long waiting periods occur. Local disturbances of the infiltration are likewise to be avoided. All of this is to be achieved, if possible, without additional structural outlay. The production costs of the inhaler component should likewise not be increased.

This object is achieved by the characterizing features of Claim 1. Accordingly, the inhaler component is provided with a second capillary gap, which holds the second end section of the wick. The wick is thus supplied with the liquid material from two sides. As a result, the waiting period for complete infiltration of the wick can be at least halved as compared with a conventional one-sided supply. If one considers that the infiltration of the wick with the liquid material takes place in a degressive-proportional manner, i.e. comparatively rapidly at the beginning and then more slowly, then it becomes clear that the waiting period for the complete infiltration of the wick by the arrangement according to the invention can be shortened by significantly more than 50%. Similarly advantageous effects result regarding the security of supply of the wick: the particularly endangered regions of the wick on the periphery in relation to the first capillary gap can now be reliably supplied with the liquid material over a short distance from the second capillary gap.

In a preferred embodiment of the invention it is provided that the first and second capillary gaps are connected to each other by a third capillary gap. The first and second capillary gaps thus communicate with each other via the third capillary gap. Thus any uneven supply of the first and second capillary gap with the liquid material can be equalized, and the security of supply to the wick further improved.

It is further provided according to the invention that one of the capillary gaps is coupled or capable of being coupled by capillary to a liquid container containing the liquid material. This capillary gap can for example be the first capillary gap. In this case the second capillary gap would be supplied with the liquid material exclusively via the third capillary gap. In addition, it could alternatively be provided that the third capillary gap is coupled or capable of being coupled by capillary to the liquid container. In this case the first and second capillary gaps would be supplied with the liquid material via the third capillary gap.

Conditions which are particularly simple structurally result if all the capillary gaps are situated in a common plane. A further structural simplification is obtained by all the capillary gaps being formed by a board, preferably a printed circuit board, and an upper section mounted on the board. In this case only two components are required to form all the capillary gaps.

In a first variant of embodiment the upper section has, according to the invention, a recess facing the board. The recess forms the capillary gaps in co-operation with the surface of the board, the depth of the recess setting the width of the capillary gaps. It is particularly advantageous for the recess to be bounded at least locally by one or more ventilation grooves. The ventilation grooves have the advantageous effect that the liquid material stored in the capillary gaps can be used more effectively as buffer volumes.

In a second alternative variant of embodiment the upper section is mounted on the end sections of the wick. The end sections of the wick act in this case as spacers which set the width of the capillary gaps. In this alternative variant of embodiment too, the upper section would be considered as being "mounted on the board", even if the two components do not touch each other directly.

The board is preferably designed in the form of a printed circuit board and it serves as such for supplying electrical energy to the—in this case—electric heating element. In this case it is particularly advantageous for the printed circuit board to be designed in the form of a multiple-layer, so-called multilayer, printed circuit board. As a result, the conductive strips supplying the electric current can in this case be concentrated in layers which do not affect the capillary gaps. In addition, more complex arrangements of conductive strips can also be implemented by means of multilayer printed circuit boards, a circumstance which proves advantageous at the latest when a plurality of electric heating elements are provided, and the heating elements are to be actuated independently of one another. Finally, on account of the multiple-layer arrangement of their conductive strips, multilayer printed circuit boards allow comparatively high electric currents to be transmitted.

In a further arrangement of the invention it is provided that the first capillary gap is coupled or is capable of being coupled to a first liquid container containing the liquid material and the second capillary gap is coupled or is capable of being coupled to a second liquid container containing the liquid material. By providing two liquid containers essentially independent of each other the security of supply of the wick with the liquid material can once again be increased.

Expedient and advantageous embodiments of the invention are illustrated in the drawings and are explained in greater detail in the following description.

In the drawings

Figure 1:
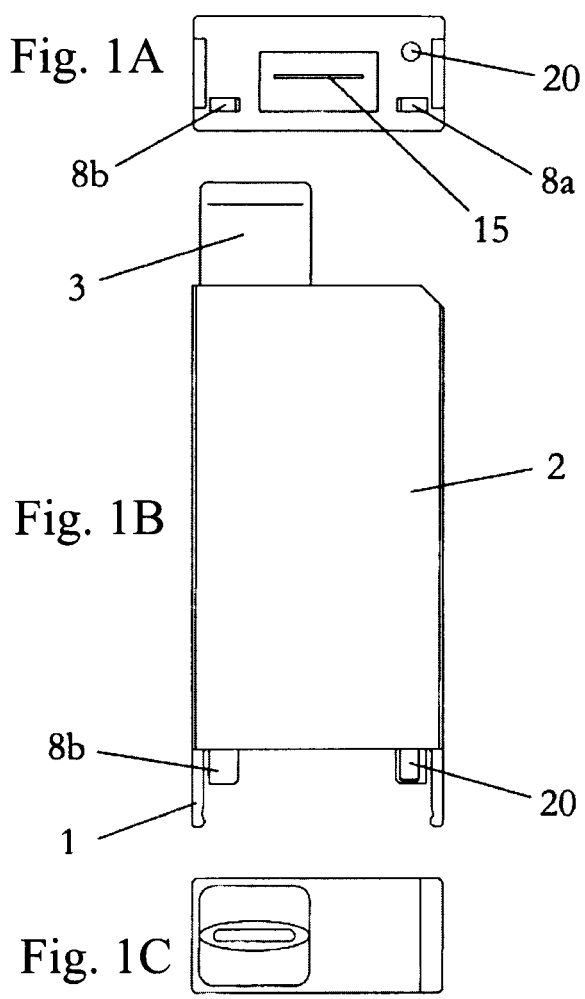
FIG. 1A shows a bottom view of an exemplary inhaler component according to the invention.
FIG. 1B shows a front view of an exemplary inhaler component according to the invention.
FIG. 1C shows a top view of an exemplary inhaler component according to the invention.

FIGS. 1A through 1C show multiple views of a first embodiment of an inhaler component according to the invention. The inhaler component in the specific example is designed in the form of an interchangeable part of the inhaler and is capable of being coupled via a snap connection 1 to a reusable inhaler part (not further shown). The inhaler component together with the reusable in haler part forms the inhaler. The inhaler component consists of a housing 2 and further comprises a mouthpiece 3, by way of which the user of the inhaler draws the vapour-air mixture or/and the condensation aerosol.

FIGS. 2 to 5 provide further information about the internal structure of the inhaler component. Thus a carrier plate 4, which is preferably designed as a printed circuit board, is located in the housing 2. The printed circuit board 4 carries a laminar composite 5. The laminar composite 5 consists of a wick 7 and an electric heating element 6, which are connected to each other in a laminar manner or integrated one into the another. The laminar composite 5 can be formed for example by a metal foil with metal fabric layers sintered on it. The laminar composite 5 can alternatively also consist of an open-pored metal foam. The open-pored capillary structure of the fabric layers sintered onto the metal foil or the metal foam forms the wick 7 and the electrical resistance of the metal forms the heating element 6. Suitable metallic resistant materials are, for example, high-grade steels such as AISI 304 or AISI 316 as well as heat-conducting alloys, in particular NiCr alloys.

The wick 7 and the laminar composite 5 containing it have two end sections 7a and 7b arranged at a distance from each other. The laminar composite 5 is mounted with these end sections on the printed circuit board 4. The laminar composite 5 is furthermore electrically contacted in the region of the end sections 7a and 7b on conductive strips of the printed circuit board 4. The electrical contacting of the laminar composite 5 or the resistance heating element 6 thereof may, for example, consist of an adhesive joint by means of an electrically conducting adhesive, for example, by means of a silver-containing adhesive based on epoxide. The printed circuit board 4 projects from the outside surface of the housing 2 in the form of two plug contacts 8a and 8b. The two plug contacts 8a and 8b serve to introduce the electrical energy into the inhaler component. The electrical energy is supplied to the electrical resistance heating element 6 via conductive strips of the printed circuit board 4. The printed circuit board 4 is preferably designed in the form of a multiple-layer, so-called multilayer, printed circuit board. The conductive strips are thus present in several layers. The advantages of this special type of printed circuit board have already been described above. The electrical energy is preferably drawn from the reusable inhaler part. For this purpose the reusable inhaler part contains a battery and an electrical control circuit for controlling the energy supply.

An upper section 9 having a recess or depression 10 is placed flat on the printed circuit board 4—see FIGS. 3 to 8B. The recess 10 is shown as a black area in FIG. 8B and has a depth of typically 0.2 mm. The recess to faces the printed circuit board 4 and, in conjunction with the surface thereof, forms a capillary gap. The capillary gap is shown diagrammatically in FIG. 2 as a black area and consists of three sections: a first capillary gap 11a, into which the laminar composite 5 or wick 7 with its end section 7a projects; a second capillary gap 11b, into which the laminar composite 5 or wick 7 with its end section 7b projects; and a third capillary gap 11c, which connects the first capillary gap 11a to the second capillary gap 11b. The first capillary gap 11a is connected to the liquid container 12 formed by the housing 2 or arranged in it. The liquid container 12 stores a liquid material 13. The capillary forces in the capillary gap 11a pull the liquid material 13 from the liquid container 12 into the capillary gap 11a. The liquid material 13 first reaches the end section 7a of the laminar composite 5. There the liquid material 13 moistens the capillary structure of the wick 7, after which the wick 7 can be further infiltrated from this side with liquid material 13. In parallel with this the liquid material 13 flows into the capillary gap 11c and finally arrives by way of the latter at the capillary gap 11b, where in the end section 7b it again moistens the capillary structure of the laminar composite 5 or the wick 7. The wick 7 is thus infiltrated from two sides with the liquid material 13. Since the flow resistance of the capillary gaps is substantially lower than the flow resistance of the wick 7, the infiltration of the wick 7 takes place at almost the same time or symmetrically on both sides. Compared with arrangements with only one-sided supply of the wick 7 (see WO 2010/045671) the infiltration time can be substantially reduced.

After the wick 7 or laminar composite 5 has been completely infiltrated with the liquid material 13, the electrical energy can be supplied to the electrical resistance heating element 6 by way of the conductive strips of the printed circuit board 4 and the liquid material 13 evaporated. To ensure as far as possible that the conductive strips do not affect the capillary gaps, it is advantageous if the conductive strips are arranged primarily on the back of the printed circuit board 4 and, if necessary, in intermediate layers (multilayer printed circuit board), and the individual conductive strips interconnected appropriately according to the state of the art by means of so-called plated-through holes. The vapour released is mixed in a chamber 14 provided in the housing 2 with the air supplied from the environment through an air intake opening 15 (see FIGS. 3 to 5) and forms the vapour-air mixture or/and condensation aerosol, which can then be transferred to a user via the mouthpiece 3.

Figure 2:
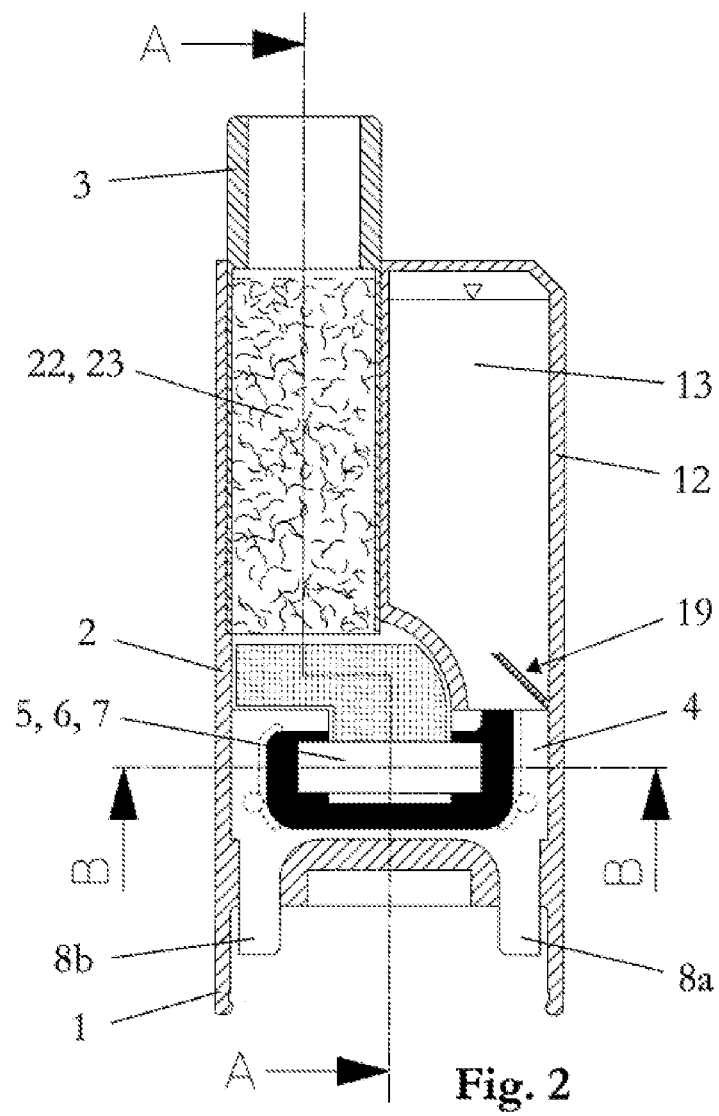
FIG. 2 is a longitudinal section through the inhaler component according to FIG. 1B at the level of the laminar composite.
Figure 4:
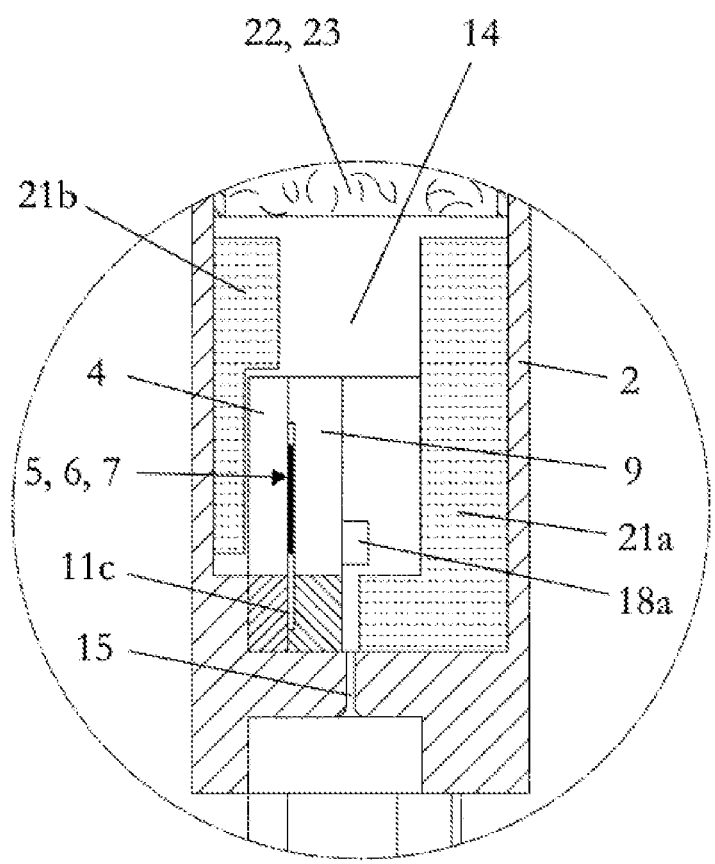
FIG. 4 shows the detail a from FIG. 3 in an enlarged view.
Figure 5:
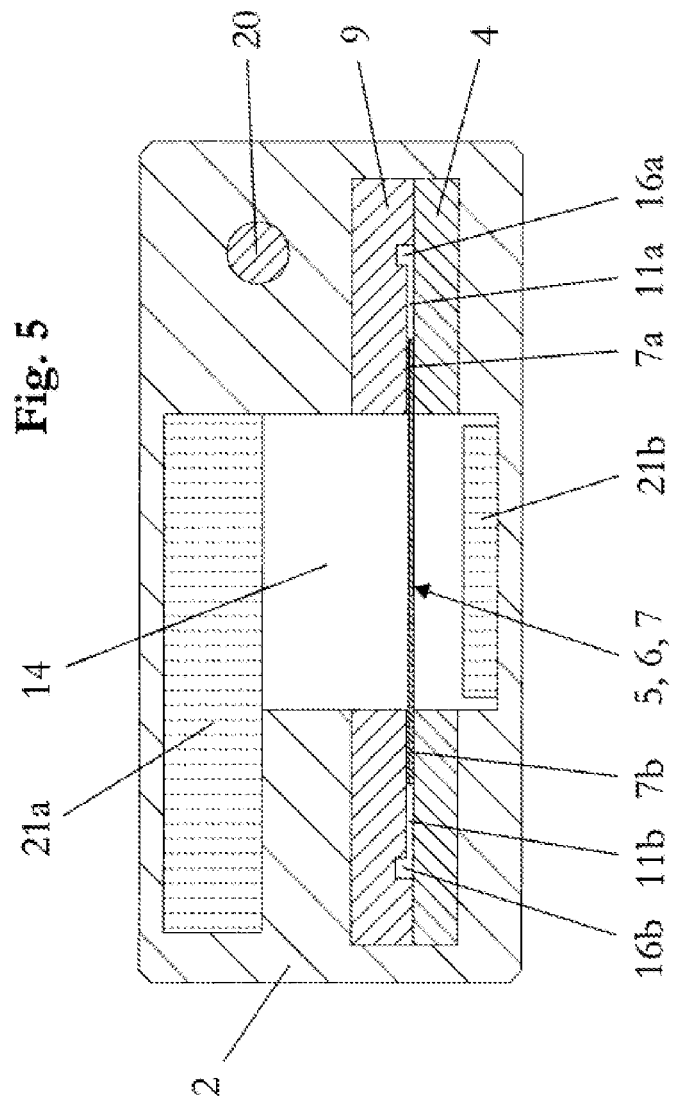
FIG. 5 is a cutaway view of the inhaler component along the line B-B in FIG. 2.
Figure 6:
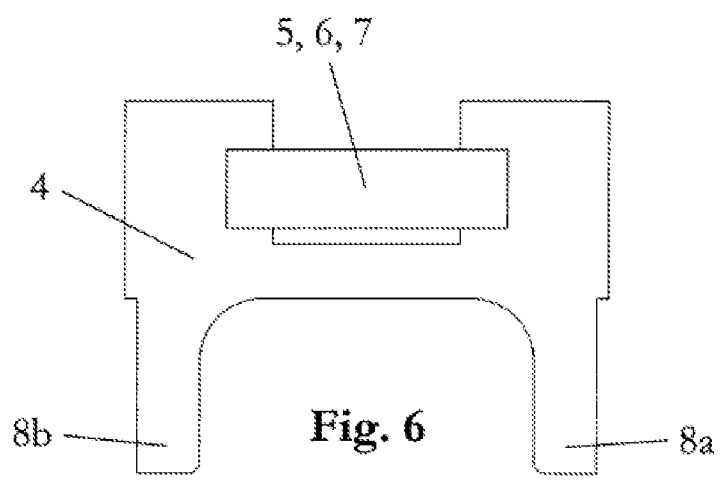
FIG. 6 shows the printed circuit board including a laminar composite.
Figure 7:
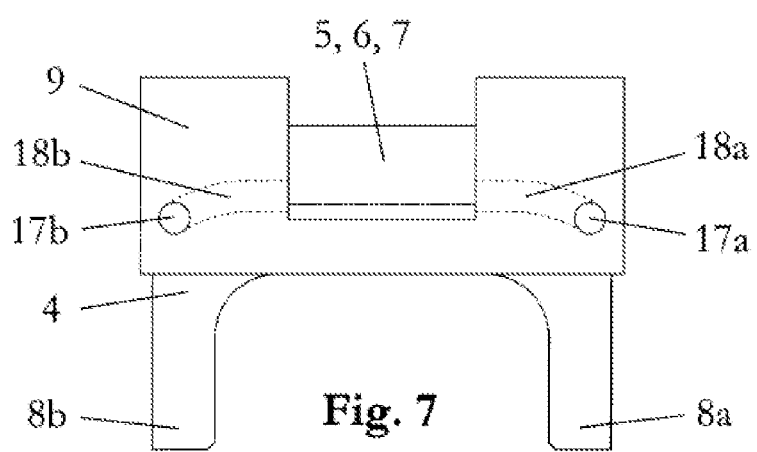
FIG. 7 shows the printed circuit board including a laminar composite joined to the upper section forming the capillary gaps.
Figure 8:
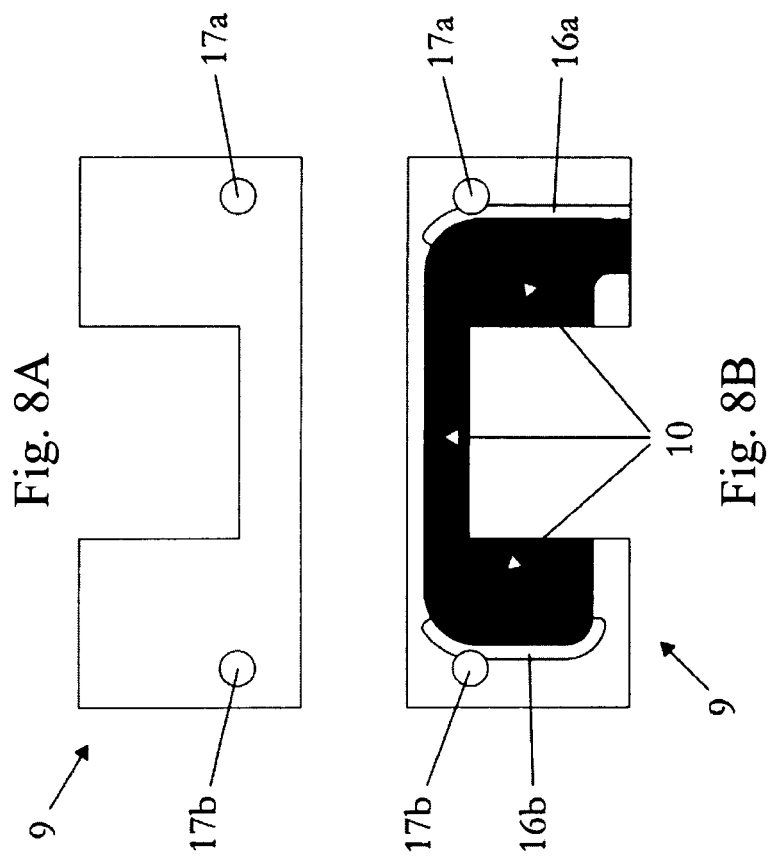
FIG. 8A shows a view of the upper section forming the capillary gaps.
FIG. 8B shows a further view of the upper section forming the capillary gaps, with the capillary gaps and recess visible.

In accordance with FIGS. 8A and 8B, the recess to in the upper section 9 is bounded in the region of the first capillary gap 11a by a first ventilation groove 16a and in the region of the second capillary gap 11b by a second ventilation groove 16b. In FIG. 2 the ventilation grooves 16a and 16b are represented diagrammatically as broken lines and in FIG. 5 are shown in cross-section. The ventilation groove 16a extends up to the liquid container 12 and ensures that each volume of liquid material 13 removed from the liquid container 12 is replaced by an equivalent volume of air. The ventilation slots 16a and 16b draw in the air via ventilation holes 17a and 17b which are formed by the upper section 9 and which for their part are connected to the chamber 14 via connecting channels 18a and 18b formed by the housing 2. The connecting channels 18a and 18b are shown diagrammatically in FIG. 7 as broken lines. The outlet of the connecting channel 18a into the chamber 14 is shown in FIG. 4.

In principle, all known printed circuit board materials are suitable as the material for the printed circuit board 4, in particular the material types FR1 to FR5. The upper section 9 is added to the printed circuit board 4 by adhesive bonding and likewise consists preferably of a plastic. It is important that the surfaces of the printed circuit board 4 as well as of the upper section 9 are well moistened by the liquid material 13. It is preferable for highly diluted ethanol or/and aqueous solutions to be used as the liquid material 13, in which the actual active substances, aerosol-forming materials, flavourings, as well as, if necessary, further ancillary materials are dissolved or/and emulsified. The wettability as well as the adhesion of the plastics can be substantially improved by surface activation, for example by hydrophilization by means of plasma polymerization (the company Diener electronic GmbH+Co. KG, www.plasma.de).

Figure 9:
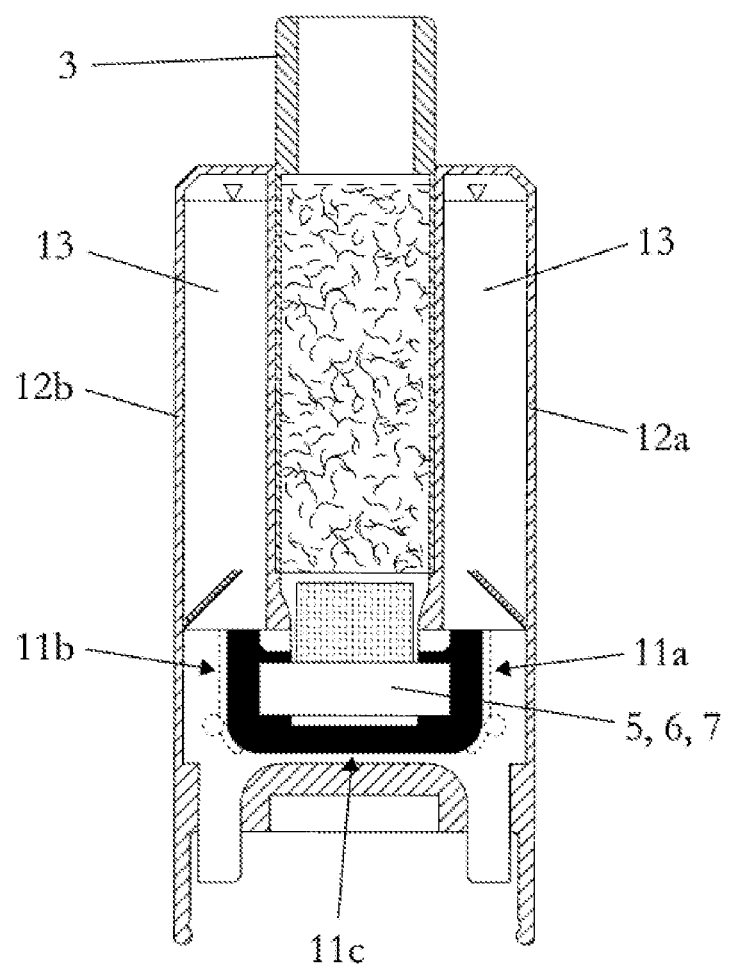
FIG. 9 shows an inhaler component according to the invention in an alternative embodiment in a view similar to FIG. 2.

FIG. 9 shows an alternative embodiment of the inhaler component according to the invention. This embodiment differs from the arrangement according to FIG. 2 essentially in that a second liquid container 12b containing the liquid material 13 is provided, which is coupled or is capable of being coupled to the second capillary gap 11b. If a disturbance of the liquid supply occurs in the first supply path (liquid container 12a and capillary gap 11a), then the laminar composite 5 or the wick 7 thereof can still be adequately supplied with liquid material 13 via the second supply path (liquid container 12b, capillary gap 11b and, if necessary, capillary gap 11c).

Figure 3:
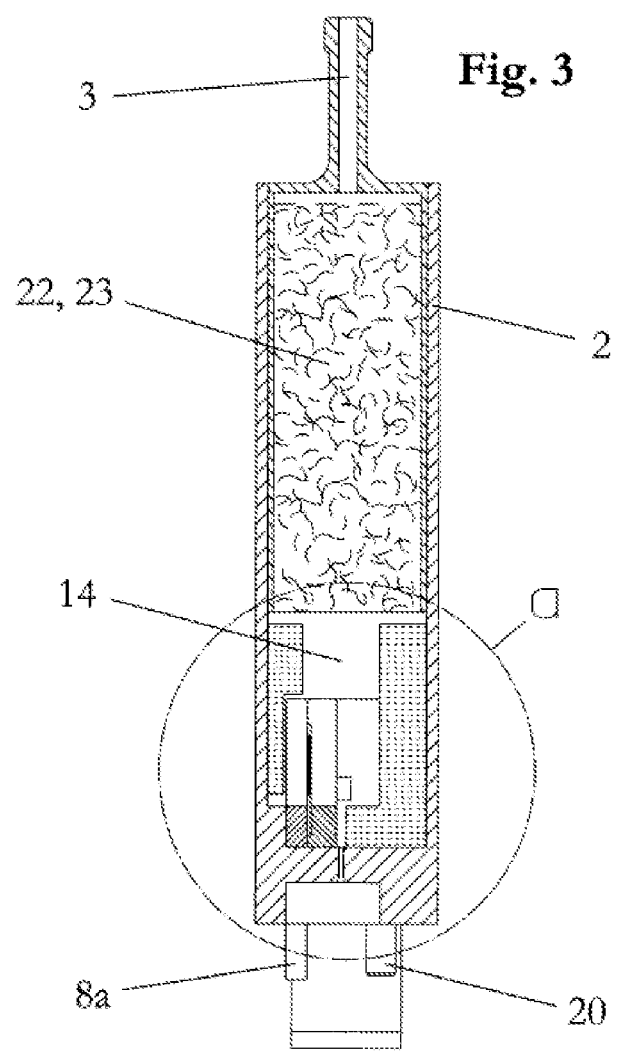
FIG. 3 is a cutaway view of the inhaler component along the line A-A in FIG. 2.

Still further components of the inhaler component are briefly described below. Even if these components are not directly relevant to the invention, their description nevertheless contributes to a better understanding of the function of the inhaler component according to the invention as a whole and ensures the workability of the invention still more certainly: as shown in FIG. 2, for example, the liquid container 12 has a valve-like, openable catch 19 on a front face. The openable catch 19 seals the liquid container 12 hermetically off from the exterior in its closed position. Only after opening the openable catch 19 can the liquid material 13 moisten the capillary gap 11a and then, through the action of capillary forces in the capillary gap, penetrate further to the laminar composite 5 and finally infiltrate the wick 7 of the laminar composite 5. The openable catch 19 is opened with the aid of a pin 20 mounted in the housing 2 in an axially adjustable manner (FIG. 3 and FIG. 5). A first end of the pin 20 is directed towards the openable catch 19. A second end extends from the outer surface of the housing 2 like an extension with the catch 19 still closed. The second end of the pin 20 is connected to the reusable inhaler part in a tappet-like operating condition. In the course of the coupling of the inhaler component with the reusable inhaler part the pin 20 is shifted into the housing 2, as a result of which the first end of the pin 20 presses against the openable catch 19. The openable catch 19 has a material weakening around its periphery which is dimensioned in such a way that when pressure is applied by the pin 20 it tears like a pre-determined breaking point over a substantial region of its periphery, but forms a hinge on one side. In this way the openable catch 19 is caused to open like a flap.

FIGS. 2 to 5 further show a condensate-binding device arranged in the chamber 14 consisting of two open-pored, absorbent sponges 21a and 21b. The sponges 21a and 21b absorb into their pores condensate deposits formed from the vapour phase and prevent freely mobile accumulations of condensate from forming in the inhaler component, in particular in the chamber 14, which could impair the function of the inhaler component and, in addition, could represent a risk for the user and the environment, if these accumulations contained drug residues or poisons such as nicotine. The two sponges 21a and 21b to a large extent line the inner walls of the chamber 14, where the sponge 21a extends up to the outlet of the air intake opening 15. In this way the condensate deposits should be prevented from reaching the relatively narrow slot-shaped air intake opening 15, as a result of which the air flow could be obstructed. In an alternative arrangement the air intake opening 15 could also be formed directly by the sponges 21a and 21b. The sponges 21a and 21b preferably consist of fine-pored, highly porous fibre composites. The company Filtrona Richmond Inc., www.filtronaporoustechnologies.com, specializes in the production of such fibre composites, in which both triacetin-bonded cellulose acetate fibres and thermally bonded polyolefin and polyester fibres are used.

As shown in FIGS. 2 to 3, a cooler 22 is provided downstream of the sponges 21a and 21b, which in the specific embodiment is integrated into the preferably interchangeable mouthpiece 3 and consists of a porous wadding 23, through the pores of which the vapour-air mixture or/and condensation aerosol formed flow. The cooler 22 cools the vapour-air mixture or/and condensation aerosol flowing through it and during this withdraws still further condensate from it. In this way the organoleptic characteristics of the vapour-air mixture or/and condensation aerosol taken up by the user can be significantly improved. The wadding 23 can consist for example of a tobacco filling. Such a tobacco filling additionally produces a flavouring of the vapour-air mixture or condensation aerosol flowing through it and is particularly desirable if the liquid material 13 contains nicotine.

Finally, it should be pointed out that the invention is naturally not limited to a laminar composite 5 in accordance with the embodiments just described. The composite could just as well have a linear format. Furthermore, the composite could also be formed from a plurality of composites or composite sections arranged next to one another, where it is immaterial how the individual composites or composite sections are electrically interconnected to one another. In this connection it should be noted that by means of the multilayer printed circuit board 4 according to the invention both series connections and parallel connections as well as more complex wiring and actuation arrangements can be effected. Finally, the invention also covers devices in which the heating element is arranged separate from the wick. For example, the wick could be formed as a laminate and the heating energy transferred to the wick by electromagnetic waves, in particular radiant heat or microwaves.

LIST OF REFERENCES 1 snap connection
2 housing
3 mouthpiece
4 carrier plate, printed circuit board
5 laminar composite
6 heating element, resistance heating element
7 wick
7a, 7b end sections of the wick or composite
8a, 8b plug contacts
9 upper section
10 recess
11a first capillary gap
11b second capillary gap
11c third capillary gap
12 liquid container
12a first liquid container
12b second liquid container
13 liquid material
14 chamber
15 air intake opening
16a, 16b ventilation slots
17a, 17b ventilation holes
18a, 18b connecting channels
19 openable catch
20 pin
21a, 21b sponges
22 cooler
23 wadding

The invention claimed is:

1. An inhaler component for the formation of at least one of a vapour-air mixture and a condensation aerosol by evaporating a liquid material, comprising:
   a heating element for the evaporation of a portion of the liquid material;
   a wick for the automatic supply of the heating element with the liquid material, said wick having at least two end sections arranged at a distance from each other;
   a first capillary gap for automatically supplying the wick with the liquid material, wherein a first end section of the wick extends into the first capillary gap; and
   a second capillary gap which holds the second end section of the wick.

2. The inhaler component according to claim 1, wherein the first and second capillary gaps are connected to each other by a third capillary gap.

3. The inhaler component according to claim 2, wherein one of the capillary gaps is one of coupled and capable of being coupled by capillary to a liquid container containing the liquid material.

4. The inhaler component according to claim 1, wherein all the capillary gaps are arranged in a common plane.

5. The inhaler component according to claim 4, wherein all the capillary gaps are formed by a board and an upper section mounted on the board.

6. The inhaler component according to claim 5, wherein the upper section has a recess facing the board.

7. The inhaler component according to claim 6, wherein the recess is bounded at least locally by at least one ventilation slot.

8. The inhaler component according to claim 5, wherein the upper section is mounted on the end sections of the wick.

9. The inhaler component according to claim 5,
   wherein the board comprises a printed circuit board; and
   wherein the printed circuit board is a multiple-layer printed circuit board.

10. The inhaler component according to claim 1, wherein the first capillary gap is one of coupled and capable of being coupled to a first liquid container containing the liquid material, and the second capillary gap is one of coupled and capable of being coupled to a second liquid container containing the liquid material.

11. An inhaler, comprising:
   an inhaler component comprising:
      a heating element for the evaporation of a portion of a liquid material;
      a wick for the automatic supply of the heating element with the liquid material, said wick having at least two end sections arranged at a distance from each other;
      a first capillary gap for automatically supplying the wick with the liquid material, wherein a first end section of the wick extends into the first capillary gap; and a second capillary gap which holds the second end section of the wick.

12. The inhaler according to claim 11, wherein the first and second capillary gaps are connected to each other by a third capillary gap.

13. The inhaler according to claim 12, wherein one of the capillary gaps is one of coupled and capable of being coupled by capillary to a liquid container containing the liquid material.

14. The inhaler according to claim 11, wherein all the capillary gaps are arranged in a common plane.

15. The inhaler according to claim 14, wherein all the capillary gaps are formed by a board and an upper section mounted on the board.

16. The inhaler according to claim 15, wherein the upper section has a recess facing the board.

17. The inhaler according to claim 16, wherein the recess is bounded at least locally by at least one ventilation slot.

18. The inhaler according to claim 15, wherein the upper section is mounted on the end sections of the wick.

19. The inhaler according to claim 15, wherein the board comprises a printed circuit board.

20. The inhaler according to claim 19, wherein the printed circuit board is a multiple-layer printed circuit board.

21. The inhaler according to claim 11, wherein the first capillary gap is one of coupled and capable of being coupled to a first liquid container containing the liquid material, and the second capillary gap is one of coupled and capable of being coupled to a second liquid container containing the liquid material.

22. The inhaler component according to claim 5, wherein the board comprises a printed circuit board.

\* \* \* \* \*